United States Patent
Petersen et al.

(10) Patent No.: US 6,392,060 B2
(45) Date of Patent: May 21, 2002

(54) METHOD FOR THE PREPARATION OF 5-CYANOPHTHALIDE

(75) Inventors: Hans Petersen, Vanløse; Poul Dahlberg Nielsen, Vig, both of (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 09/888,067

(22) Filed: Jun. 22, 2001

Related U.S. Application Data

(63) Continuation of application No. PCT/DK99/00728, filed on Dec. 22, 1999.

(30) Foreign Application Priority Data

Dec. 23, 1998 (DK) .................................... 1998 01718

(51) Int. Cl.⁷ ............................................ C07D 307/87
(52) U.S. Cl. .................................... 549/307; 549/304
(58) Field of Search ................................ 549/307, 304

(56) References Cited

U.S. PATENT DOCUMENTS

| | | | |
|---|---|---|---|
| 3,467,675 A | 9/1969 | Petersen et al. | 260/346.2 |
| 4,136,193 A | 1/1979 | Bogeso et al. | 424/285 |
| 4,650,884 A | 3/1987 | Bogeso | 549/467 |
| 4,943,590 A | 7/1990 | Boegesoe et al. | 415/469 |
| 6,020,501 A | 2/2000 | Massonne et al. | 549/307 |
| 6,028,204 A | 2/2000 | Massonne et al. | 549/307 |
| 6,229,026 B1 | 5/2001 | Petersen | 549/467 |
| 6,258,842 B1 | 7/2001 | Petersen et al. | 514/469 |
| 6,291,689 B1 | 9/2001 | Petersen et al. | 549/467 |

FOREIGN PATENT DOCUMENTS

| | | | |
|---|---|---|---|
| EP | 0 171 943 A1 | 2/1986 | |
| EP | 0 474 580 | 3/1992 | A61K/31/34 |
| EP | 1 095 926 | 5/2001 | C07C/33/46 |
| WO | 98/19511 | 5/1998 | |
| WO | 98/19512 | 5/1998 | |
| WO | 9819513 A2 | 5/1998 | |
| WO | 98/28293 | 7/1998 | C07D/401/04 |
| WO | 99/30548 | 6/1999 | |
| WO | 00/11926 | 3/2000 | |
| WO | 00/12044 | 3/2000 | |
| WO | 00/13648 | 3/2000 | |
| WO | 00/23431 | 4/2000 | C07D/307/87 |
| WO | 00/39112 | 7/2000 | C07D/307/87 |
| WO | 00/44738 | 8/2000 | C07D/307/88 |

OTHER PUBLICATIONS

U.S. Patent Application Serial No. 09/794,762, filed Feb. 26, 2001.
U.S. Patent Application Serial No. 09/794,755, filed Feb. 26, 2001.
U.S. Patent Application Serial No. 09/830,109, filed Jun. 1, 2001.
U.S. Patent Application Serial No. 09/891,874, filed Jun. 25, 2001.
U.S. Patent Application Serial No. 09/917,180, filed Jul. 27, 2001.
U.S. Patent Application Serial No. 09/692,653, filed Oct. 18, 2000.
U.S. Patent Application Serial No. 09/930,107, filed Aug. 14, 2001.
U.S. Patent Application Serial No. 09/930,110, filed Aug. 14, 2001.
U.S. Patent Application Serial No. 09/977,920, filed Oct. 15, 2001.
U.S. Patent Application Serial No. 10/012,054, filed Nov. 6, 2001.
U.S. Patent Application Serial No. 10/012,025, filed Nov. 6, 2001.
Levy, L.F., "4–Aminophthalide and Some Derivatives", *J. Chem. Soc.* pp. 867–870, (1931).
Tirouflet J., "Phtalide Substitutes en 5", *Bull. Soc. Sci. de Bretagne*, 26:35–43 (1951).
Perregaard, Jens et al., "σ Ligands with Subnanomolar Affinity and Preference for the σ₂ Binding Site 1. 3–(ω–Aminoalkyl)–1H–indoles," *J. Med. Chem.* 38:1998–2008 (1995).
Bigler, Allen et al., "Quantitative structure–activity relationship in a series of selective 5–HT uptake inhibitors", *Eur. J. Med. Chem.*, 3:289–295 (1977).
Buehler, Calvin A. et al., "Survey of Organic Syntheses," *Wiley–Interscience*, John Wiley & Sons, Inc., p. 951 (date unavailable).
Barton, Sir Derek, F.R.S. et al., *Comprehensive Organic Chemistry. The Synthesis and Reactions of Organic Compounds*, vol. 2, pp. 1024–1025. (date unavailable).

*Primary Examiner*—Patricia L. Morris
(74) *Attorney, Agent, or Firm*—Darby & Darby

(57) ABSTRACT

A method for the preparation of 5-cyanophthalide in which 5-carboxyphthalide is converted to the corresponding amide of Formula (IV)

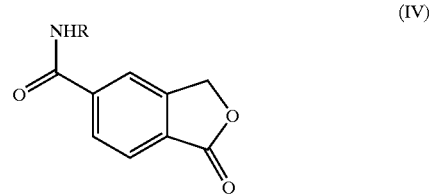

(IV)

in which R is hydrogen or $C_{1-6}$ alkyl, which is then reacted with a dehydrating agent thereby obtaining 5-cyanophthalide. The conversion of 5-carboxyphthalide to the corresponding amide of Formula (IV) may be carried out via the corresponding $C_{1-6}$ alkyl or phenyl ester or the acid chloride, which is converted to the amide of Formula (IV) by amidation with ammonia or a $C_{1-6}$ alkylamine. By the process 5-cyanophthalide, an important intermediate used in the preparation of the antidepressant citalopram, is prepared in high yields by a convenient, cost effective procedure.

17 Claims, No Drawings

METHOD FOR THE PREPARATION OF 5-CYANOPHTHALIDE

This is a continuation of international application Serial No. PCT/DK99/00728, filed Dec. 22, 1999, the entire disclosure of which is hereby incorporated by reference.

The present invention relates to a novel process for the preparation of 5-cyanophthalide which is an intermediate used in the manufacture of the well known antidepressant drug citalopram, 1-[3-(dimethylamino)propyl]-1-(4-fluorophenyl)-1,3-dihydro-5-isobenzofurancarbonitrile.

BACKGROUND OF THE INVENTION

Citalopram is a well known antidepressant drug that has now been on the market for some years and has the following structure:

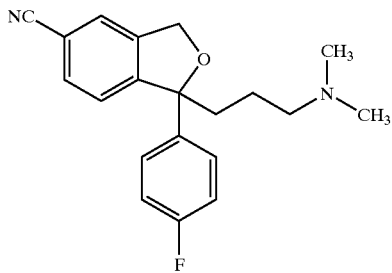

Formula I

It is a selective, centrally active serotonin (5-hydroxytryptamine; 5-HT) reuptake inhibitor, accordingly having antidepressant activities. The antidepressant activity of the compound has been reported in several publications, eg. J. Hyttel, Prog. *Neuro-Psychopharmacol. & Biol. Psychiat.*, 1982, 6, 277–295 and A. Gravem, *Acta Psychiatr. Scand.*, 1987, 75, 478–486.

Citalopram is prepared by the process described in U.S. Pat. No. 4,650,884, according to which 5-cyanophthalide is subjected to two successive Grignard reactions, i.e. with 4-fluoro-phenyl magnesium halogenide and N,N-dimethylaminopropyl magnesium halogenide, respectively, and the resulting compound of the formula

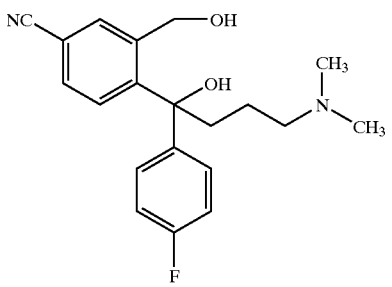

Formula II is subjected to a ring closure reaction by dehydration with strong sulfuric acid.

Enantiomers of citalopram may be prepared by the method described in U.S. Pat. No. 4,943,590, i.e. by separating the enantiomers of the intermediate of Formula II and performing enantioselective ring closure in order to obtain the desired enantiomer.

Thus, 5-cyanophthalide is an important intermediate for the manufacture of citalopram and it is important to produce this material in an adequate quality, by a convenient process and in a cost-effective way.

A method for the preparation of 5-cyanophthalide has previously been described in Bull. Soc. Sci. Bretagne, 26, 1951, 35 and in Levy and Stephen, J. Chem. Soc., 1931, 867. By this method, 5-aminophthalide is converted to the corresponding 5-cyanophthalide by diazotation followed by reaction with CuCN. 5-Aminophthalide was obtained from 4-aminophthalimide by a two step reduction procedure.

Synthesis of certain alkyl- and phenylnitriles from acid chlorides is described in Tetrahedron Letters, 1982, 23, 14, 1505–1508, and in Tetrahedron, 1998, 54, 9281.

Though a number of other methods failed, it has been found that 5-cyanophthalide may be prepared in high yields by a convenient, cost-effective procedure from 5-carboxyphthalide.

DESCRIPTION OF THE INVENTION

Accordingly, the present invention provides a novel method for the preparation of 5-cyanophthalide from 5-carboxyphthalide comprising a) converting 5-carboxyphthalide to an amide of Formula IV

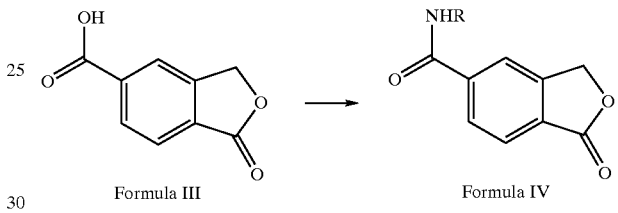

Formula III          Formula IV in which R is hydrogen or $C_{1-6}$ alkyl, and b) then reacting the amide of Formula IV with a dehydrating agent thereby obtaining 5-cyanophthalide

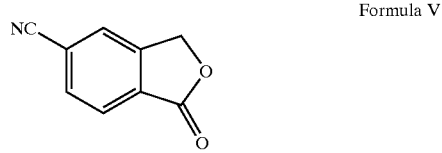

Formula V

The conversion of 5-carboxyphthalide to the amide of Formula IV may be carried out via an ester of Formula VI or an acid chloride of Formula VII or via the ester and the acid chloride:

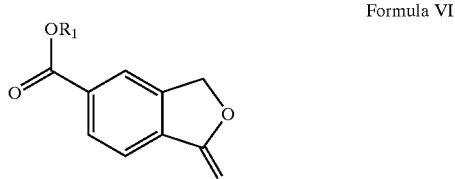

Formula VI

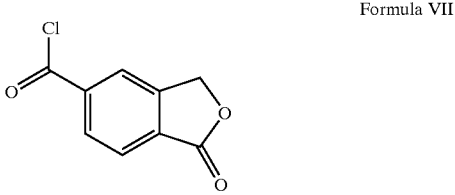

Formula VII wherein $R_1$ is $C_{1-6}$ alkyl or phenyl. The acid chloride is conveniently obtained by treatment of 5-carboxyphthalide with $POCl_3$, $PCl_5$ or $SOCl_2$ neat or in a suitable solvent, such as toluene or toluene comprising a catalytic amount of N,N-dimethylformamide. The ester is obtained by treatment of 5-carboxyphthalide with an alcohol $R_1OH$, wherein $R_1$ is as defined above, in the presence of an acid, preferably a mineral acid or a Lewis acid, such as HCl, $H_2SO_4$, $POCl_3$, $PCl_5$ or $SOCl_2$. Alternatively, the ester may be obtained from the acid chloride by reaction with an alcohol. The ester of Formula VI or the acid chloride of Formula VII is then converted to the amide of Formula IV by amidation with ammonia or an $C_{1-6}$ alkylamine, preferably t-butyl amine.

Throughout the specification and Claims, $C_{1-6}$ alkyl refers to a branched or unbranched alkyl group having from one to six carbon atoms inclusive, such as methyl, ethyl, 1-propyl, 2-propyl, 1-butyl, 2-butyl, 2-methyl-2-propyl, 2,2-dimethyl-1-ethyl and 2-methyl-1-propyl.

The dehydrating agent used in step b) may be any suitable dehydrating agent, and the optimal agent may easily be determined by a person skilled in the art. Examples of suitable dehydrating agents are $SOCl_2$, $POCl_3$ and $PCl_5$, preferably $SOCl_2$.

The reaction in step b) is carried out neat or in a suitable solvent, such as toluene, sulfolan or conveniently acetonitrile. When the reaction is carried out in a solvent, 1.0–1.5, preferably 1.0–1.2 equivalents of dehydrating agent is used per equivalent of the amide of Formula V. Furthermore, when a solvent is used, a catalytic amount of N,N-dimethylformamide may be needed, in particular when the dehydrating agent is $SOCl_2$. Preferably, toluene is used as the solvent, if necessary in the presence of a catalytic amount of N,N-dimethylformamide.

The reaction in step b) is carried out at elevated temperature, preferably at the reflux temperature of the solvent.

The reaction time is not important and may easily be determined by a person skilled in the art.

5-Cyanophthalide may be isolated in a conventional way, e.g. by addition of water, filtration and subsequent washing of the crystals. Further purification may, if desired, be performed by recrystallisation.

In a preferred embodiment of the process of the invention, R in Formula IV is H or t-butyl. When the reaction in step a) is carried out via an ester, $R_1$ is preferably methyl or ethyl.

In a particularly preferred embodiment of the invention 5-carboxyphthalide of Formula III is reacted with an alcohol, $R_1OH$, preferably ethanol, in the presence of $POCl_3$, in order to obtain the corresponding ester of Formula VI, which is then reacted with ammonia thereby giving 5-carbamoylphthalide, which in turn is reacted with $SOCl_2$ in toluene comprising a catalytic amount of N,N-dimethylformamide.

Surprisingly, substantially no reaction takes place at the lactone ring. Accordingly, by the process of the invention, 5-cyanophthalide is obtained in high yields and the process is much more convenient than the known process and uses more convenient and cheaper reactants and conditions.

The 5-carboxyphthalide used as a starting material may be obtained by the methods described in U.S. Pat. No. 3,607,884 or German patent No. 2630927, i.e. by reacting a concentrated solution of terephthalic acid with formaldehyde in liquid $SO_3$ or by electrochemical hydrogenation of trimellithic acid.

EXAMPLES

The invention is further illustrated by the following examples.

Example 1

Preparation of 5-Cyanophthalid

5-Chlorocarbonylphthalid

5-Carboxyphthalid (53 g, 0.3 mole) was suspended toluene (200 mL) and thionylchloride (44 g, 0.6 mole). N,N-dimethylformamide (DMF) (1 mL) was added and the mixture was heated at reflux temperature for 3 hours. The mixture was cooled to room temperature and n-heptane was added (200 ml). The crystals formed were collected and washed with heptane (100 mL). Yield 52 g, 88%. DSC onset: 131° C. $^1H$ NMR (CDCl$_3$, 500 MHz): 5.47 (2H, s), 8.06 (1H, d, J=7.5 Hz), 8.28(1H, d, J=7.5 Hz), 8.3(1H, s). $^{13}C$ NMR (CDCl$_3$, 125 MHz): 69.4, 125.1, 126.1, 131.1, 131.6, 137.8, 146.6, 167.4, 169.0.

5-tert.Butylcarbamylphthalid

Method A):

5-Carboxyphthalid (36 g, 0.2 mole) was suspended in thionylchloride (100 mL). DMF (1.5 mL) was added and the mixture was refluxed for 1 hour. Toluene (200 mL) was added and the solvents were evaporated in vacuo. The residue was dissolved in tetrahydofuran (THF) (200 mL) and added to a solution of tert.butylamine (31 g, 0.42 mole) in THF (200 mL) at 5° C. The mixture was allowed to warm to room temperature and stirred overnight. The reaction was then poured into ice water (400 mL) and the precipitated crystals were filtered off. The crystals were washed with water (100 mL) Yield: 41 g, 87%. DSC onset: 189.5° C.

Method B):

A solution of 5-chlorocarbonylphthalid (39 g, 0.2 mole) in THF (200 mL) was added to a solution of tert-butylamine (19 g. 0.25 mole) and triethylamine (26 g, 0.25 mole) in THF (200 mL) at room temperature. The mixture was stirred for 1 hour. The reaction mixture was then poured into ice water (500 mL). The crystalline material formed was collected and washed with water (100 mL). Yield 42.5 g, 91%. DSC onset: 192° C. Purity: 99.5% (hplc, peak area). $^1H$ NMR (DMSO-d$_6$, 500 MHz): 1.4 (9H, s), 5.46 (2H, s), 7.88 (1H, d, J=7.5 Hz), 7.95 (1H, d, J=7.5 Hz), 8.04 (1H, s). $^{13}C$ NMR (DMSO d$_6$, 125 MHz): 28.5, 51.2, 70.0, 122.0, 124.6, 126.6, 128.2, 141.3, 147.2, 165.5, 170.1.

5-Ethoxycarbonylphthalid

Method A):

5-Carboxyphthalid (37 g, 0.2 mole) was suspended in ethanol (400 mL). POCl$_3$ (10 g, 0.07 mole) was added drop-wise and the reaction mixture was heated to reflux temperature for 5 hours. Upon cooling to room temperature, the title compound crystallised. The crystals were filtered off and washed with ethanol (50 ml). Yield: 35 g, 87%. DSC onset: 151° C. $^1H$ NMR (DMSO-d$_6$, 250 MHz): 1.36 (3H, t, J=7 Hz), 4.38 (2H, q, J=7 Hz), 5.48 (2H, s), 7.95 (1H, d, J=7.5 Hz), 8.12 (1H, d, J=7.5 Hz),. $^{13}C$ NMR (DMSO-d$_6$, 62.5 MHz): 14.5, 61.5, 70.1, 124.0, 125.2, 128.8, 129.6, 134.8, 147.6, 164.9, 169.8.

Method B):

5-Chlorocarbonylphthalid (39 g, 0.2 mole) was suspended in ethanol (200 mL). The mixture was heated to reflux for 15 minutes. After cooling, the crystalline material formed was filtered of and washed with ethanol (50 ml). Yield: 36 g, 88%. DSC onset: 151° C.

5-Carbamylphthalid

Method A):

5-Ethoxycarbonylphthalid (41 g, 0.2 mole) was suspended in ammonia (10M solution in methanol, 200 mL) in a pressure reactor. The reaction temperature was held at 80° C. for 20 hours. After cooling, the reaction mixture was poured onto ice (250 g) and pH was adjusted to pH=1 using concentrated hydrochloric acid. The mixture was stirred for 2 hours. The crystals formed were filtered off and washed with water (4×100 mL) and dried in vacuo. Yield: 33 g, 93%. DSC onset: 237° C. $^1H$ NMR (DMSO-d$_6$, 250 MHz): 5.47

(2H, s), 7.65 (1H, s (NH)), 7.92 (1H, d, J=7.5 Hz), 8.06 (1H, d, J=7.5 Hz), 8.14 (1H s), 8.22 (1H, s (NH)). $^3$C NMR (DMSO-$d_6$, 62.5 MHz): 70.0, 122.2, 124.9, 127.2, 128.2, 139.7, 147.4, 167.1, 170.1.

Method B):

5-Chlorocarbonylphthalid (20 g, 0.1 mole) was dissolved in THF (100 mL) and added to ammonium hydroxide (50 mL) in ice water (300 mL). The mixture was stirred for 30 minutes and the precipitated crystals were filtered off. The crystals were washed with water (100 mL) and dried in vacuo. Yield: 17.1 g, 97%. DSC onset: 237° C.

5-Cyanophthalid

Method A):

Dry 5-carbamylphthalid (36 g, 0.2 mole) was suspended in toluene (600 mL) and thionyl-chloride (36 g, 0.3 mole) was added. DMF (2 mL) was added. The reaction mixture was heated at 75° C. for 6 hours. Toluene (100 mL) was removed by distillation and the remaining solution was cooled to room temperature. The crystals formed were filtered off and washed with toluene (150 mL) and water (100 mL). The product was recrystallised from toluene. Yield: 22 g, 80%. DSC onset:203° C.

Method B):

Tert.-Butylcabamylphthalid (23.3 g, 0.1 mole) was suspended in thionylchloride (100 mL). The mixture was heated to reflux for 30 min. Toluene (100 mL) was added and the solvents were removed in vacuo. The title product was crystallised from acetic acid or toluene. Yield 15.5 g, 93% from toluene. DSC onset: 203° C. Purity: 98% (hplc, peak area).

What is claimed is:

1. A method for the preparation of 5-cyanophthalide comprising a) conversion of a 5-carboxyphthalide to an amide of Formula IV

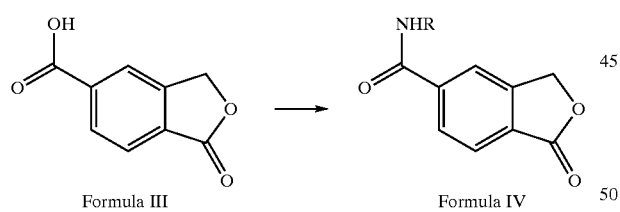

in which R is hydrogen or $C_{1-6}$ alkyl, and b) then reacting the amide of Formula IV with a dehydrating agent thereby obtaining 5-cyanophthalide

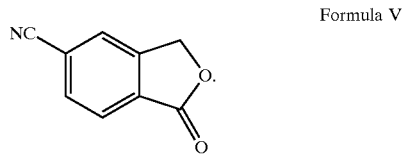

2. The method of claim 1, wherein the conversion of 5-carboxyphthalide to the amide of Formula IV is carried out via an ester of Formula VI:

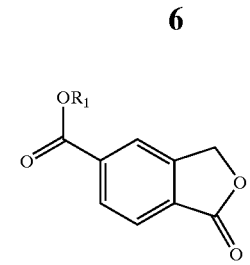

wherein $R_1$ is $C_{1-6}$ alkyl or phenyl, by treatment of 5-carboxyphthalide with an alcohol $R_1$OH in the presence of an acid and subsequent amidation of the ester of formula VI with ammonia or a $C_{1-6}$ alkylamine.

3. The method of claim 1, wherein the conversion of 5-carboxyphthalide to the amide of Formula IV is carried out via an acid chloride of Formula VII:

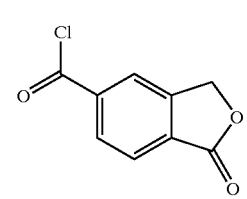

by treatment of 5-carboxyphthalide with POCl$_3$, PCl$_5$ or SOCl$_2$ and subsequent amidation of the acid chloride of Formula VII with ammonia or a $C_{1-6}$ alkylamine.

4. The method of claim 1, wherein the conversion of 5-carboxyphthalide to the amide of Formula IV is carried out via an acid chloride of Formula VII and an ester of Formula VI:

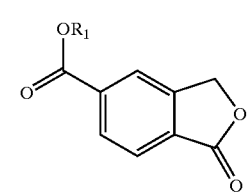

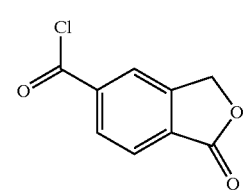

wherein $R_1$ is $C_{1-6}$ alkyl or phenyl, by treatment of 5-carboxyphthalide with POCl$_3$, PCl$_5$ or SOCl$_2$, reaching the acid chloride of Formula VII thus formed with an alcohol $R_1$OH and performing amidation of the ester of Formula VI with ammonia or a $C_{1-6}$ alkylamine.

5. The method of claim 2, wherein the acid used is a mineral acid or Lewis acid.

6. The method of claim 5, wherein the mineral acid or Lewis acid is selected from the group consisting of HCl, H$_2$SO$_4$, POCl$_3$, PCl$_5$ and SOCl$_2$.

7. The method of claim 2, 4 or 5, wherein $R_1$ is methyl or ethyl.

8. The method of claim 1, in which the dehydrating agent used in step b) is SOCl$_2$, POCl$_3$ or PCl$_5$.

9. The method of claim 8, in which the dehydrating agent is SOCl$_2$.

10. The method of claim 1, wherein the reaction in step b) is carried out neat or in a suitable solvent.

11. The method of claim 10, wherein the reaction is carried out in a solvent selected from the group consisting of toluene, sulfolan or acetonitrile.

12. The method of claim 11, wherein the solvent is toluene.

13. The method of claim 10, wherein the dehydrating agent used in step b) is $SOCl_2$ and the reaction is carried out in toluene comprising a catalytic amount of N,N-dimethylformamide.

14. The method of claim 1, wherein R is H or tert-butyl.

15. The method of claim 2, wherein the 5-carboxyphthalide of Formula III is reacted with an alcohol $R_1OH$, in the presence of $POCl_3$, in order to obtain an ester of Formula VI, which is then reacted with ammonia, thereby giving 5-carbamoyl-phthalide, which in turn is reacted with $SOCl_2$ to 5-cyanophthalide.

16. The method of claim 15, wherein the alcohol $R_1OH$ is ethanol or methanol.

17. The method of claim 15, wherein the 5-carboxyphthalide of Formula III is reacted with ethanol in the presence of $POCl_3$, in order to obtain the ethyl ester of Formula VI, which is then reacted with ammonia in methanol, thereby giving 5-carbamoylphthalide, which in turn is reacted with $SOCl_2$ to 5-cyanophthalide.

* * * * *